United States Patent [19]

Murphy

[11] Patent Number: 5,409,376
[45] Date of Patent: Apr. 25, 1995

[54] APPARATUS AND PROCESS FOR LASER-ASSISTED DRILING

[76] Inventor: Quentin M. Murphy, 77 Pondsfield Rd., Bronxville, N.Y. 10708

[21] Appl. No.: 29,233

[22] Filed: Mar. 10, 1993

[51] Int. Cl.⁶ ............................................. A61C 1/00
[52] U.S. Cl. ..................................... 433/29; 408/701;
606/10; 433/215; 433/165
[58] Field of Search ................. 433/29, 114, 119, 125,
433/165, 166, 215; 607/89; 606/7, 10, 11, 80;
408/16, 22, 24, 701; 219/121.67, 121.69

[56] References Cited

U.S. PATENT DOCUMENTS

| | | | |
|---|---|---|---|
| 3,696,504 | 10/1972 | Cupler, II | 408/701 |
| 4,126,136 | 11/1978 | Auth et al. | 219/121.67 |
| 4,356,376 | 10/1982 | Komanduri et al. | 219/121.69 |
| 4,506,745 | 3/1985 | Bjor | 175/45 |

FOREIGN PATENT DOCUMENTS

| | | | |
|---|---|---|---|
| 0375578 | 6/1990 | European Pat. Off. | 433/29 |
| 0125954 | 9/1980 | Japan | 408/16 |

*Primary Examiner*—Cary E. O'Connor
*Attorney, Agent, or Firm*—Fitzpatrick, Cella, Harper & Scinto

[57] ABSTRACT

Apparatus and process of laser assisted drilling includes structure and method for receiving laser energy and projecting it onto an object to produce structural changes within the object. Structure and method are also provided for mechanically abrading the structurally perturbed portions of the object. By combining laser and mechanical energy, drilling is quickly and accurately performed.

40 Claims, 2 Drawing Sheets

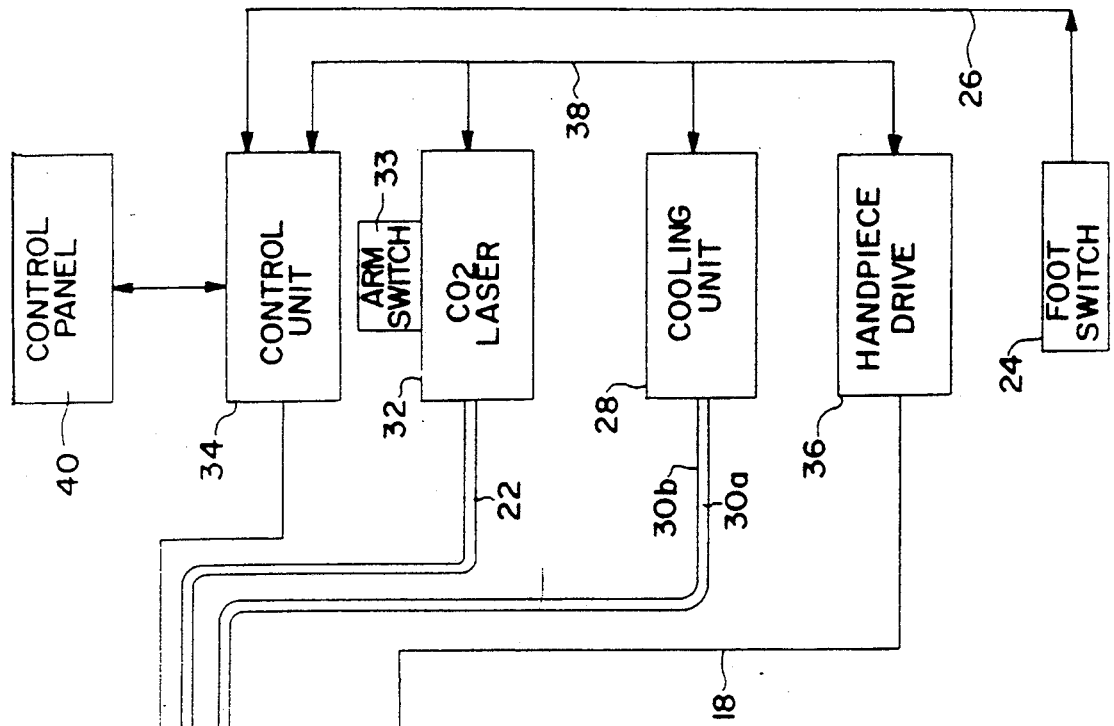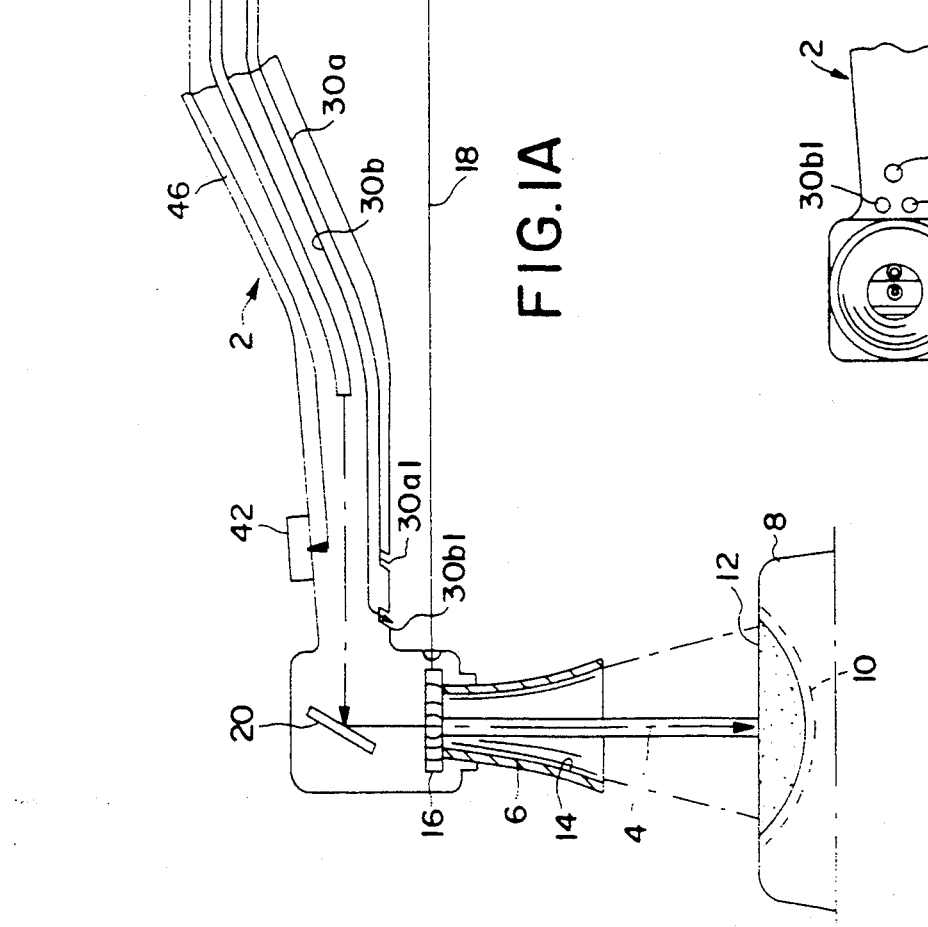

APPARATUS AND PROCESS FOR LASER-ASSISTED DRILING

BACKGROUND OF THE INVENTION

1. Field of the Invention

The present invention relates generally to apparatus and process for laser-assisted drilling, and more particularly to laser-assisted drilling which utilizes laser energy to alter the molecular structure of an object and then utilizes mechanical action to abrade the altered structure to remove it from a given site. While the present invention has particular application to a laser assembly suited for dental applications, the teachings of this invention may be applicable to other drilling systems.

2. Description of the Prior Art

Laser assemblies are known to be used in dental procedures such as the eradication of carious lesions (removal of dental decay), treatment of sensitive teeth, removal off soft tissue, enamel, etc., and for restorative work, etc. In all known dental applications, laser energy is used directly and unassisted, either by focused beam or through an optical point, for removing the unwanted material and/or altering the tooth structure. U.S. Pat. No. 4,818,230 to Myers, et al., discloses such a system in which pulsed laser energy is aimed at the tooth decay and repeatedly applied until the decay is eradicated from the tooth. The laser is a yttrium-Aluminum-Garnet (YAG) laser having a pulsewidth of 50–2000 microns, a pulse duration of a picosecond to several milliseconds, and an energy of 0.1–100 millijoules.

U.S. Pat. No. 4,940,411 to Vassiliadis, et al., is another known dental laser system in which a Neodymium doped yttrium-Aluminum-Garnet (Nd:YAG) laser is used to eliminate; the unwanted material, and a helium-neon (HeNe) laser is used as a pointing device to illuminate the area to be removed by the more powerful Nd:YAG laser. The Nd:YAG laser has a pulse repetition rate of between 1 and 10,000 pulses per second, an average power of up to 50 watts, a pulse duration of between 1 picosecond and several milliseconds, and a peak energy of up to 5 joules per pulse.

One difficulty with all such known dental laser devices is that the dentist has no tactile sensation for controlling the drilling process. That is, the dentist does not have the "feel" for how much and what type of material is being eliminated from the tooth. With known mechanical dental drills, the dentist can apply the correct amount of pressure to the correct location, and can also feel what effect the drill is having on the tooth. Thus, with a mechanical dental drill, the dentist's hand becomes a very effective force applicator and an extremely fine sensor. Without this contact with the tooth, as with known laser dental systems, the dentist can no longer accurately apply energy to the tooth or sense the tooth structure, itself, by "feel".

Another problem with known dental laser systems applied to hard tissues is safety. Application of laser energy sufficient to remove hard tooth structure by ablation may cause some damage in soft tissues if the laser accidentally strays or is reflected from an instrument such as a dental mirror.

Yet a further problem with known dental laser systems is long-term patient comfort. Known high-power dental lasers may cause gross thermal damage to the tooth, damaging the dental nerve. This is especially true since it is quite difficult to control the depth of laser-induced change with a known laser device working on tooth structure.

Yet another problem with known dental laser systems is their high cost. Most dentists already possess a mechanical dental drill, and to purchase and install a laser system which does not also safely reduce hard dental tissues will require a great deal of additional space, time, and expense.

While the above-noted drawbacks of dental laser systems have thus far prevented their universal acceptance in hard-tissue dentistry, the well-known problems of noise, vibration, and pain associated with mechanical dental drills have produced a pronounced aversion to dental visits among many patients. Therefore, what is needed is an entirely new dental drilling modality which combines the advantages of both the laser and mechanical drilling systems.

SUMMARY OF THE INVENTION

The present invention overcomes the above-noted problems of both laser and mechanical drills by combining their features into a single laser-assisted drill. Laser energy and mechanical energy are combined in one drill to both weaken and remove the tooth structure. Preferably, $CO_2$ laser energy is directed through the interior of a dental drill onto the tooth. The laser energy (either pulsed or continuous wave) is modulated to cause the tooth structure to recrystallize into a chalky, charred, easily-removed material. The mechanical portion of the drill bur is then used to easily remove the structurally perturbed portion of the tooth. Thus, the laser energy is used to change the molecular structure of the tooth while the dentist still preserves his/her tactile sense for actually removing the structure. This combination of laser energy and mechanical energy also permits the laser to be of lower power than known systems, thus reducing cost and safety concerns.

Another advantage of the combination of laser and mechanical energy is that either energy form may be used by itself. That is, the dentist might still use the laser without the mechanical drill for performing other procedures such as coagulation, gingival sculpting, etc. Yet, a mechanical drill bur may be used by itself to perform procedures such as conventional drilling, etc. Thus, with one device the dentist obtains the advantages of a laser system, a mechanical dental drill, and the synergistic effects of the combined laser/mechanical system.

According to one aspect of the present invention, a laser-assisted drill comprises means for receiving laser light; and head means, coupled to the receiving means, for directing the laser light onto an object to be drilled. The head means includes drill means for mechanically abrading the object onto which the laser light has been directed.

According to another aspect of the present invention, a laser drill comprises directing means for receiving laser light and directing it to an object to cause a structural perturbation therein. Drill means are disposed adjacent the directing means, for removing the perturbed structure from the object.

According to a further aspect of the present invention, a laser-assisted dental drill comprises a hand-piece; and a waveguide, disposed within or attached to the hand-piece, for receiving light energy and transmitting it along a transmission path. Directing means are coupled to the waveguide means, for receiving the transmitted light energy and directing it to a tooth to disturb, perturb, or alter a structural arrangement thereof. A drill is disposed adjacent or surrounding the directing means, for contacting the tooth and removing the structurally disturbed portions thereof.

According to a still further aspect of the present invention, a laser drill bit comprises directing means for receiving light energy and directing it to an object to perturb a structural arrangement thereof; and drill means, disposed adjacent or surrounding the directing means, for removing structurally disturbed portions of the object.

In yet a further aspect of the present invention, a method of laser-assisted drilling comprises the steps of projecting laser energy onto an object to perturb a structural arrangement thereof; and drilling the object to remove the structurally perturbed portions thereof.

In yet a further aspect of the present invention, a method of performing laser-assisted dental drilling comprises the steps of receiving laser energy in a dental hand-piece; reflecting the laser energy toward a tooth to cause structural changes in the tooth; and physically removing the structurally changed portion of the tooth with a drill bit.

BRIEF DESCRIPTION OF THE DRAWINGS

The above-noted advantages and features of the present invention will be better understood from the following detailed description of the preferred embodiments taken in conjunction with the following Drawings which show:

FIG. 1A is a block diagram of a laser-assisted dental drill according to a preferred embodiment of the present invention, and FIG. 1B is a bottom view of a portion of the hand-piece 2 of FIG. 1A;

DETAILED DESCRIPTION OF THE PREFERRED EMBODIMENTS

Figure 2A:
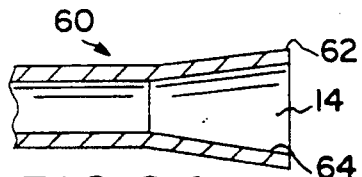
FIGS. 2A, 2B, and 2C respectively show a cross-sectional side view, an end view, and a laser energy pattern of a first drill bit according to the present invention.

The basic concept of the present invention is one of using laser energy to transform tooth, bone, or other structure (such as concrete) to a weaker state that can be removed mechanically. Laser energy can be provided from any known energy source, including $CO_2$ lasers, and the mechanical energy can be derived from known mechanical drill burs, ultrasound, high-pressure water, reciprocating impact devices, particle-blasters (e.g., alumina or sand-blasters), diamond saws, etc.

According to the dental drill embodiment, the laser energy is used to weaken and restructure the hydroxy-apatite crystalline substance which forms within selected collagenous matrices that form the hard structures of the body (tooth and bone). Experimentally, evidence has shown that the $CO_2$ laser, used at certain pulse frequencies and intensities, can cause a weakening and a restructuring of the hydroxy-apatite crystals within the matrix of dental enamel which has a Brinnell hardness of 7 (equivalent to the hardness of opal). The present embodiment capitalizes on this phenomenon by first allowing the laser energy to accomplish the weakening and restructuring of the hydroxy-apatite, and then using some form of mechanical energy to remove the weakened structure.

While the present embodiment is particularly directed to a dental use of the laser-assisted drill, it is known that other hydrated substances, such as gypsums, cements used in concrete, and certain rocky deposits will also more easily be broken down using the same concept of applying laser energy to alter the molecular state of an object, and then mechanically abrading away the structurally perturbed portion of the object.

FIG. 1A is a block diagram of a laser-assisted dental drill according to a preferred embodiment of the present invention. In FIG. 1, a hand-piece 2 is used to direct both laser energy 4 and the drill bit 6 toward the tooth 8. The laser energy 4 is directed by the dentist toward an area 10 of the tooth 8 to produce a molecularly-disturbed area 12 in which the hydroxy-apatite crystals within the dental enamel/or dentinal matrix are weakened. If $CO_2$ laser energy is used, the tooth enamel will be recrystallized into a flaky structure at one intensity level, but will be melted and solidified at another intensity level; preferably the dentin will be recrystallized to a char-like substance. The drill bit 6 is rotated through the disturbed area 12 to mechanically (and preferably) simultaneously abrade the molecularly perturbed portions of the tooth 8.

Preferably, the laser energy is derived from a $CO_2$ laser because of its apparent low-power requirements for this effect and its effects on hydrated substances. However, other known lasers such as the Nd:YAG laser discussed earlier may be used. Furthermore, the rapid advance in the development of precise and controllable lasers will suggest other acceptable lasers to those of skill in this field, such as Homium/YAG, Erbium, Excimer, etc.

In the preferred embodiment, the drill bit 6 is a conventional dental drill which has been adapted to be used in conjunction with laser energy. However, those of skill in this field will recognize that other structures for mechanically abrading the structurally perturbed portions of the tooth may be used, such as ultrasound, high-pressure water, reciprocating impact devices, sandblasting, etc.

The drill bit 6 preferably comprises a carbon-steel structure which is diamond-coated at the cutting portions. An interior passageway 14 has been provided at the center of the drill bit 6 to allow passage of the laser energy therethrough. Preferably, the passageway 14 is interior-coated with a reflective substance in order to provide optimum propagation of the laser energy through the drill bit 6.

In FIG. 1, the hand-piece 2 also includes a turbine 16 which is used to rotate the drill bit 6. In one form, the turbine 16 is a conventional air turbine driven by compressed air provided through a driver transmission path 18. A side advantage of the conventional dental air turbine 16 is that air may be used to cool both the drill bit 6 and the tooth 8. Thus, additional air may be directed downward over (or through) the drill bit 6 toward the tooth 8, as in conventional dental drilling.

The hand-piece 2 also preferably includes a mirror 20 which reflects laser energy 4 from a laser waveguide 22 down through the turbine 16, through the drill bit 6, and to the tooth 8. In an alternative form, the mirror 20 may be eliminated and the laser waveguide 22 may be bent downward to direct its energy through the turbine 16, the drill bit 6, and toward the tooth 8, for those laser wavelengths which propagate accordingly.

As shown in FIG. 1B, the hand-piece 2 may also include conventional air cooling ports 30$b$1 and 30$b$2 fed by air transmission hose 30$b$; and a water port 30$a$1 fed by water hose 30$a$.

The hand-piece 2 is controlled by foot switch 24 which includes various control switches (not shown) for controlling, inter alia: the rotational speed of drill bit 6; the application of laser energy; and the application of cooling air and/or water. Preferably, the foot switch 24 is a conventional dental foot switch which has been modified so that laser energy is provided through the passageway 14 when the drill bit 6 reaches a predetermined threshold rpm, e.g., 1000–500,000 RPM. The foot switch 24 is coupled to control unit 34 via an electrical cable 26.

The control unit 34 is also coupled to $CO_2$ laser 32, the cooling unit 28, and the hand-piece drive 36 through bus 38. The $CO_2$ laser unit 32 provides laser energy, as described above, if its associated arm switch 33 has been activated and the drill bit 6 has reached its predetermined threshold rpm. However, any convenient and desirable method for controlling the application of laser energy may be incorporated in the present invention. For example, slide switch 42 may be provided on the hand-piece 2 to control various drilling and cooling functions through cable 46 and control unit 34.

The control unit 34 is also coupled to a control panel 40 which may display operational information such as whether the laser is on or off, the laser power level, pulse repetition rate, pulse width, and other information. The control panel 40 may also display status information for the cooling unit 28, the drill driver 36, and the hand-piece 2.

The hand-piece drive 36 provides power through a transmission path 18 to rotate or drive the drill bit 6. The hand-piece drive 36 may comprise an air-pump, a liquid pump or an electrical motor for driving the drill bit 6 through a series of belts, pulleys, gears, etc. The art of driving a dental drill is developed well enough so as to require no further elucidation at this time.

The cooling unit 28 provides a coolant liquid or air/water spray through the transmission hoses 30$a$ and 30$b$ into the hand-piece 2 and then downward toward the tooth 8 via the ports 30$a$1, 30$b$1, and 30$b$2. While it is believed that some laser energies will not require the use of a cooling unit, it will be helpful in most instances where laser energy and high-speed drilling are used. Additionally, the use of coolant air and/or water spray may assist in clearing debris from the drilling site. Additional cooling air may be derived from the air which drives the turbine 16. That is, where hand-piece drive 36 comprises an air-pump, the air which drives turbine 16 may be directed downward through passageway 14 within drill bit 6 to provide additional cooling air. Furthermore, by directing air downward through passageway 14, dust build-up which may occur within the drill bit 6 may be prevented, thus ensuring little or no adhesion of dust and debris on the internal reflective surfaces of the drill bit 6.

FIGS. 2–7 show a variety of different drill bits (dental burs) which may be applied to the present invention. Note that all of these configurations show the laser energy propagating through the center of the drill bur. However, the laser energy may be directed beside the bur, in parallel to the bur or at an angle with respect thereto. Whether the laser energy is propagated through or beside the bur, it is nevertheless "adjacent" the drill bur. Those of ordinary skill in this field may readily ascertain a number of different configurations for directing both the laser energy and the drill bur to a similar location on the tooth.

In FIG. 2A, a drill bit 60 comprises the passageway 14 and the drill bur 62. The specific structural details of the bur 62 are omitted for purposes of clarity. The wide variety of shapes and sizes of drill burs are well known to those of skill in this field. Such known burs may be adapted for use with the present invention depending on the specific purpose for which a specific drill bit 60 is intended. Preferably, the bur 62 is coated with a diamond or other abrasive texture to enhance the cutting operation. Preferably, the passageway 14 is coated with a reflective substance 64 in order to deliver as much laser power to the tooth as possible. However, the passageway 14 may be non-coated, or coated with a light modulating substance depending upon the laser power and focus desired to be delivered to the tooth. It may even be filled with a light-guiding fiber bundle.

Figure 2B:
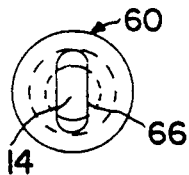
Figure 2C:
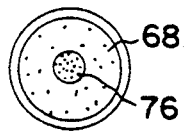

FIG. 2B is an end view of the FIG. 2A drill bit 60 used for end cuts. In FIG. 2B, the passageway 14 opens up to a race-track-like opening 66 substantially centered at the center of the drill bit 60. FIG. 2C shows a light projection pattern of the drill bit 60. A high-intensity area 76 is produced in a circular pattern at the center of the drill bit area where the laser energy is unmodulated while the drill bit 60 rotates. A lower-intensity area 68 surrounds the area 76.

Figure 3A:
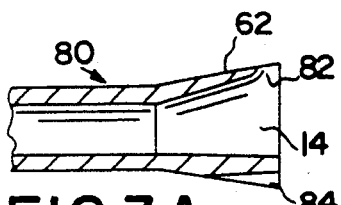
FIGS. 3A, 3B, and 3C respectively show a cross-sectional side view, an end view, and a laser energy pattern of a second drill bit according to the present invention.
Figure 3B:
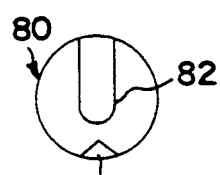
Figure 3C:
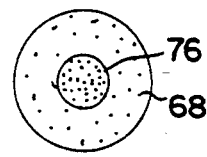

FIG. 3A depicts a cross-sectional view of a drill bit 80 also used for end cuts. The drill bit 80 also has a bur 62 and a passageway 14, but further includes a cut-out portion 84 which aids in mechanically drilling the tooth structure and in balancing the bit 80 as it rotates. The passageway 14 diverges in only one direction from the longitudinal axis of the bit 80, thus producing the race-track-like opening 82 as depicted in FIG. 3B. Since the opening 82 extends to below the longitudinal axis, the light projection pattern comprises a two-intensity pattern, as shown in FIG. 3C. In the light-projection pattern depicted in FIG. 3C, a high-intensity portion 76 is disposed at the center of the pattern where laser energy is constantly propagated. In contrast, a lower-intensity area 68 surrounds the area 76 since the laser energy sweeps over this area as the opening 82 rotates. Since the opening 82 extends through the periphery of the bit 80, the light projection area 68 is actually larger than the diameter of the bit 80.

Figure 4A:
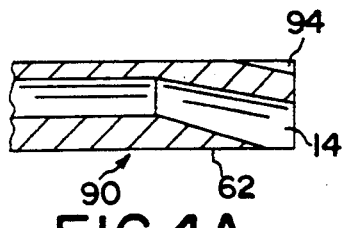
FIGS. 4A, 4B, 4C, and 4D respectively show a cross-sectional side view, an end view, and laser end and side energy patterns of a third drill bit according to the present invention.
Figure 4B:
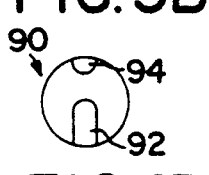
Figure 4C:
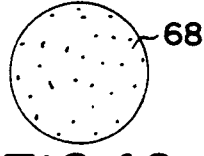
Figure 4D:
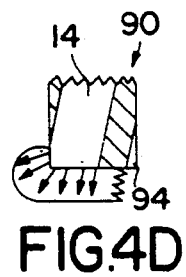

FIG. 4A is a cross-sectional view of a drill bit 90 intended for cylindrical cuts. That is, the side surfaces of the drill bit 62 are intended to perform cutting as well as the end face of the drill bit. In drill bit 90, passageway 14 is disposed in the center of the bit 90, but tapers downward to the periphery of the drill bit, as shown in FIG. 4A. A cut-out portion 94 is disposed opposite the passageway 14 to assist in cutting and to provide balance. As depicted in FIG. 4B, the resultant opening 92 extends from the center of the bit 90 to the periphery thereof. FIG. 4C shows the light-projection pattern wherein even-intensity light is projected over a wider area than the drill bit diameter. Furthermore, as can be understood from FIG. 4D, laser energy actually projects from the side of the bit 90 due to the reflection of the laser energy within passageway 14.

Figure 5A:
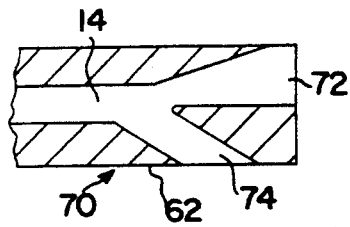
FIGS. 5A, 5B, and 5C respectively show a cross-sectional side view, an end view, and a laser energy pattern of a fourth drill bit according t-o the present invention.
Figure 5B:
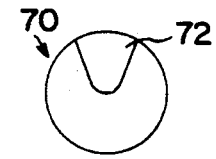
Figure 5C:
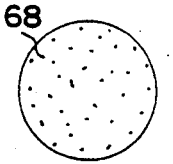

FIG. 5A depicts a cross-sectional view a drill bit 70 also intended for cylindrical cuts. The bit 70 also has a bur 62 and a passageway 14, but the passageway 14 diverges into two separate passageways 72 and 74. Passageway 72 extends to the end of bit 70, while passageway 74 projects from the side of bit 70. FIG. 5B shows that the end of bit 70 looks somewhat similar to the end of bit 90 (FIG. 4B), but does not include a cut-out portion. The light-projection pattern of bit 70 depicted in FIG. 5C also appears similar to the light projection pattern of FIG. 4C, but a significant amount of laser light also exits passageway 74 thus directing much more laser energy to the side of the bit 70 than in the case of the bit 90.

All of the drill bits 60, 70, 80, and 90 shown above are not drawn to scale or dimension, for purposes of clarity. Furthermore, those of ordinary skill in this field will readily understand that a wide variety of drill bit shapes and sizes may be designed within the scope of the present invention without departing from the material teachings thereof.

Figure 6:
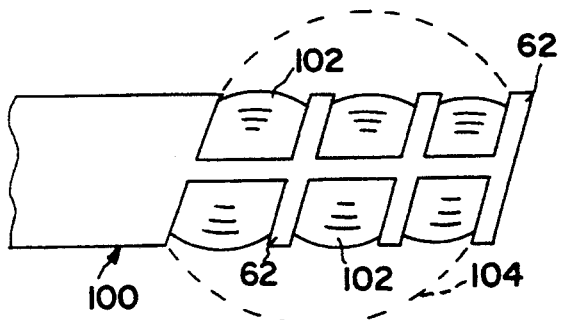
FIG. 6 is a side view of a fifth drill bit according to the present invention.
Figure 7:
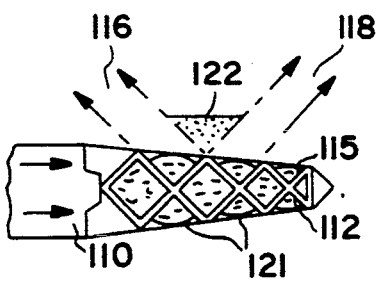
FIG. 7 is a side view of a sixth drill bit according to the present invention.

FIGS. 6 and 7 depict novel drill bits 100 and 110, respectively. In each of these embodiments, laser energy is propagated through the side of the drill bit, and cutting is preferably accomplished with a side cut rather than an end cut. Both the embodiments of FIGS. 6 and 7 feature optical lenses, or fiber tips, and/or mirrors which guide the laser energy into predetermined fields adjacent the drill bits. The laser energy may be either reflected toward the lenses by structure internal to the drill bit for subsequent propagation beyond the drill bit surface, or the laser energy may be refracted by the lenses themselves or other optical components (e.g., prisms) used in conjunction with the lenses.

In FIG. 6, the drill bit 100 comprises a helical bur 62 interspaced or surrounding one or more lenses 102. The lens or lenses 102 may comprise one integral structure having uniform or varying optical structures, or may comprise a plurality of lenses having similar or dissimilar optical properties. In the preferred form, the bur 62 is made of high hardness/high heat metal such as carbide steel while the lens or lenses 102 comprises one or more biconvex optical lenses, attached to internal waveguides such as fiber optic waveguides. The lens or lenses 102 should be configured to provide a laser energy pattern 104 which has its highest intensity adjacent the bur, and preferably from 0 to 0.5 millimeters from the surface of bur 62. The helical shape of the bur 62 provides enhanced cutting action while also acting to modulate the field intensity ore the laser energy.

The drill bit 110 shown in FIG. 7 comprises one or more biconvex optical reflectors, e.g., mirrors 121 surrounded by a pair of helical burs 112 and 115. In this embodiment, the reflectors 121 may include lenses and are configured to provide a plurality of laser propagation fields 116 and 118 which overlap at the area 122. Thus, the overlap area 122 comprises an area of higher laser intensity providing sufficient energy to recrystalize the tooth structure.

Like the bit 100, the bit 110 is intended for side-cutting applications. Of course, optical lenses may be used with any of the configurations of FIGS. 2–5, depending upon the specific application for which the drill bit is designed. Furthermore, the drill bits 100 and 110 may be attached to a reciprocating drill driver rather than a rotary driver. In such a case, the burs 62, 112, 115 may comprise circumferential rather than helical structures.

Figure 8:
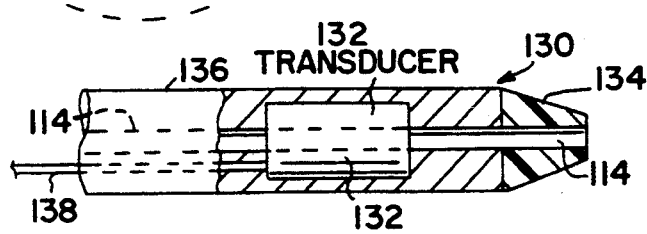
FIG. 8 is a side view of a seventh drill bit according to the present invention.

FIG. 8 depicts an ultra-sound applicator 130 which comprises a passageway 114, a transducer 132, an applicator head 134, and a supporting structure 136. As with the previously-discussed drill bits, laser energy is propagated down the passageway 114 onto the tooth 8. A transducer 132 accepts signals from the electrical cable 138 attached to the control unit 34, and the transducer 232 generates ultra-sound frequency signals which abrade and remove the structurally perturbed portions 12 of the tooth 8. The applicator head 134 may be used to physically contact tooth 8 to provide the desired tactile sensation.

In use, the dentist selects from among a plurality of interchangeable, replaceable drill bits for a particular dental procedure, and installs the selected drill bit on the hand-piece 2. The dentist then grasps the hand-piece 2, inserts it into the patient's mouth adjacent the tooth 8, and activates foot switch 24 to begin rotation of the drill and to project laser energy onto the tooth 8 when the drill has reached the predetermined RPM. Preferably, the laser energy is infrared light which produces a spot size of from 1 mm–3.5 mm on the tooth 8. The laser energy may be either pulsed or continuous wave, as discussed above. The dentist applies the drill bit 6 to the desired area 12 to disturb the molecular structure of the tooth and remove it. The dentist may drill with or without the laser energy being projected onto the tooth 8. Practice and experience will permit the dentist to use combined or alternating laser and mechanical energy to remove portions of the tooth 8, according to the particular dental procedure being carried out. When using the drill bits according to FIGS. 2–5, the laser energy is reflected from one or more reflective surfaces within the passageways 14, etc. The projected laser energy patterns may be either conical, elliptical,, spherical, or whatever shape is provided by the geometry of passageway 14.

During the drilling operations, the dentist may activate the cooling unit 28 through use of the foot switch 24, or an alternative control means provided on control panel 40. The cooling unit 28 may provide cooling air, a cooling water spray, or a combination of those fluids to produce the desired cooling effect, to cool both the drill bit 6 and the tooth 8.

Since the laser energy will quickly produce the desired structural disturbance in the tooth 8, the drill bit 6 will remove tooth structure at a very rapid rate. Therefore, the dental procedure will be quick and comfortable for the patient, removing the stigma of dental pain, drill noise, and vibration, and allowing the dentist to successfully treat many more patients.

Thus, what has been described is apparatus and method for laser-assisted drilling in which laser energy is utilized to structurally perturb an area of an object to be drilled, and the perturbed area is then mechanically removed.

The individual components shown in outline or designated by blocks in the Drawings are all well-known in the laser and drilling arts, and their specific construction and operation are not critical to the operation or best mode for carrying out the invention.

While the present invention has been described with respect to what is presently considered to be the preferred embodiments, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A laser-assisted drill comprising: means for receiving laser light;
    head means, coupled to said means for receiving laser light, for directing said laser light onto an object to be drilled, said head means including drill means for abrading the object onto which the laser light has been directed,
    a laser source for generating the laser light; and
    modulation means for modulating the laser light.

2. A drill according to claim 1, wherein said means for receiving laser light comprises a waveguide.

3. A drill according to claim 2, wherein said waveguide includes a flexible waveguide portion.

4. A drill according to claim 1, wherein said head means includes laser energy distribution means, disposed adjacent said drill means, for distributing energy from said laser light onto the object.

5. A drill according to claim 4, wherein said laser energy distribution means includes at least one light reflector disposed inside said drill means, said drill means having at least one opening therein to allow the laser light to be transmitted to the object.

6. A drill according to claim 1, wherein said drill means comprises a rotating drill bit having a helical array of interposed cutting surfaces and openings therein.

7. A drill according to claim 1, wherein said drill means includes a reciprocating drill bit.

8. A drill according to claim 1, wherein said drill means includes ultrasound means for abrading the object with ultrasound energy.

9. A drill according to claim 1, wherein said head means comprises:
    reflecting means for reflecting the laser light onto the object;
    a rotating drill, as said drill means, for abrading the object with a rotary motion; and
    turbine means for rotating said rotating drill.

10. A drill according to claim 9, wherein said reflecting means comprises a plurality of light reflecting surfaces which reflect the laser light in a plurality of directions.

11. A drill according to claim 10, wherein said plurality of reflecting surfaces are disposed inside of said rotating drill, said rotating drill having at least one opening therein through which the reflected light propagates.

12. A drill according to claim 1, further comprising driving means for driving said drill means.

13. A drill according to claim 1, wherein said head means comprises a drill bit enclosing at least one optical fiber for transmitting the laser light.

14. A laser drill comprising:
    directing means for receiving laser light and directing it to an object to cause a structural perturbation therein;
    drill means, disposed adjacent said directing means, for mechanically removing the perturbed structure from the object,
    a hand-piece for holding said directing means and said drill means; and
    driving means, disposed inside said hand-piece for causing said drill means to rotate.

15. A laser drill according to claim 14, wherein said drill means comprises a rotating drill bur, and wherein said directing means is disposed inside said rotating bur.

16. A laser drill according to claim 14, wherein said drill means comprises a plurality of interchangeable rotating drill burs.

17. A laser drill according to claim 14, wherein said directing means comprises a plurality of reflecting surfaces for reflecting the laser light in a plurality of overlapping directions.

18. A laser drill according to claim 14, wherein said directing means includes means for intensifying laser energy directed to at least one portion of the object.

19. A laser drill according to claim 18, wherein the intensifying means comprises biconvex optical means for directing the laser light in a plurality of overlapping fields, the overlapped portions of the fields including the intensified laser energy.

20. A laser-assisted dental drill comprising:
    a hand-piece;
    a waveguide, disposed within said hand-piece, for receiving light energy and transmitting it along a transmission path;
    directing means, coupled to said waveguide means, for receiving the transmitted light energy and directing it to a tooth to disturb a structural arrangement thereof; and
    a drill, disposed adjacent said directing means, for contacting said tooth and removing structurally disturbed portions thereof.

21. A dental drill according to claim 20, wherein said directing means is disposed within said drill, said drill having at least one hole therein through which the light energy passes to the tooth.

22. A dental drill according to claim 20, wherein said directing means comprises a plurality of reflecting surfaces for reflecting the light energy in a plurality of overlapping fields.

23. A dental drill according to claim 20, further comprising a laser source, coupled to said waveguides, for generating the light energy.

24. A dental drill according to claim 20, wherein said directing means and said drill are coupled together in a unitary, replaceable cartridge.

25. A dental drill according to claim 20, further comprising driving means for causing said drill to rotate, and wherein said directing means comprises a plurality of reflecting surfaces disposed within said drill.

26. A dental drill according to claim 20, wherein said drill is hollow, and further comprising means for producing a positive air flow through the hollow drill to prevent tooth debris build-up on an internal surface of said drill.

27. A laser drill bit, comprising:
    directing means for receiving light energy and directing it to an object to perturb a structural arrangement thereof; and
    drill means, disposed adjacent said directing means, for removing structurally disturbed portions of the objects,
    wherein said directing means is disposed inside said drill means, said drill means having at least one hole therein through which the light energy passes to the object, wherein said directing means comprises a plurality of reflecting surfaces for directing the light energy in a plurality of overlapping fields, and wherein said drill means comprises a cylindrical drill bur having a plurality of cutting portions, said drill bur being rotatable about a cylindrical axis thereof.

28. A drill bit according to claim 27, further comprising means for rotating said cylindrical drill bur.

29. A drill bit according to claim 27, wherein said cylindrical drill bur comprises an array of interposed cutting portions and openings through which the light energy passes to the object.

30. A dental laser drill bit comprising:
a laser energy transmission path for directing laser energy onto an object to be drilled; and
a drill bur, surrounding said transmission path, for drilling the area of the object onto which the laser energy is directed by said transmission path, said transmission path including reflecting means, disposed on an inside of said drill bur, for reflecting the laser energy onto the object to be drilled.

31. A method of laser-assisted drilling comprising the steps of:
projecting laser energy onto an object to perturb a structural arrangement thereof, said projecting step including the step of projecting the laser energy from an inside of the drill bit to an outside thereof in a radial direction; and
drilling the object to mechanically remove the structurally disturbed portions thereof, said drilling step comprising the step of contacting the object with a drill bit and mechanically abrading the disturbed portions of the object.

32. A method according to claim 31, wherein said projecting step comprises the steps of:
receiving the laser energy;
reflecting the received laser energy from a plurality of reflecting surfaces to produce a plurality of overlapping laser energy fields; and
transmitting the reflected laser energy from an inside of a drill bit to an outside thereof.

33. A method according to claim 32, wherein said drilling step comprises the steps of rotating a drill bit about the plurality of reflecting surfaces, and passing the reflected laser energy through a plurality of holes in the drill bit.

34. A method according to claim 31, wherein said projecting step includes the step of projecting a spherical field of laser energy surrounding a drill bit.

35. A method according to claim 31, wherein said projecting step includes the step of projecting a conical field of laser energy from a drill bit.

36. A method of performing laser-assisted dental drilling comprising the steps of:
receiving laser energy in a dental hand-piece;
reflecting the laser energy toward a tooth to cause structural changes in the tooth;
physically removing the structurally changed portion of the tooth with a drill bit.

37. A method according to claim 36, wherein said reflecting step includes the step of reflecting said laser energy through an interior of the drill bit.

38. A method according to claim 36, further comprising the step of cooling the tooth.

39. A method according to claim 36, further comprising the step of cooling the drill bit.

40. A method according to claim 36, wherein said step of physically removing includes the step of modulating the laser light with a rotation of the drill bit.

* * * * *